United States Patent [19]

Brill et al.

[11] Patent Number: 5,167,695
[45] Date of Patent: Dec. 1, 1992

[54] DERIVATIVES OF QUINOLINE FUSED TO A FIVE-MEMBERED HETEROCYCLIC RING

[75] Inventors: Gunter Brill, Hassloch; Helmut Hagen, Frankenthal; Karl-Otto Westphalen, Speyer; Bruno Wuerzer, Otterstadt, all of Fed. Rep. of Germany

[73] Assignee: BASF Aktiengesellschaft, Ludwigshafen, Fed. Rep. of Germany

[21] Appl. No.: 527,831

[22] Filed: May 24, 1990

[30] Foreign Application Priority Data

Jun. 1, 1989 [DE] Fed. Rep. of Germany ....... 3917883
Feb. 7, 1990 [DE] Fed. Rep. of Germany ....... 4003587

[51] Int. Cl.⁵ .................... A01N 43/72; A01N 43/34; A01N 43/64; C07D 471/02
[52] U.S. Cl. .......................................... 71/94; 71/92; 546/82; 546/83
[58] Field of Search ................ 546/82, 83; 514/293; 71/88, 92, 94

[56] References Cited

FOREIGN PATENT DOCUMENTS 090360 10/1983 European Pat. Off. .

OTHER PUBLICATIONS

Moores et al., An N→N'-Benzyl Migration . . . , J. Fluorine Chem., 88; 41(2), pp. 277-288.
Milata et al., Preparation & Spectral Properties of Imidazo- and Triazoloquinolines . . . , Collect. Czech. Chem. Commun., 88; 53(5), pp. 1068-1077.
Chimenti et al., Studies on Amine Oxidase-Inhibiting Substances . . . , Farmaco, Ed. Sci,. 87; 42(7), pp. 513-524.
*Chemical Abstracts*, vol. 107, entry 232001 (1987).
Case, Francis H., The Preparation of 2-Substituted Benzimidazole Derivatives Containing the Ferroin Group (1), J. Heterocycl. Chem., 4(1), 1967, pp. 157-159.
"Thermal Cyclocondensations of 3-N(4-And 5-Benzimidazolyl and . . . ", Milta et al., Coll. Czech. Chem. Comm., vol. 52 (1987).
Journal of Fluorine Chem., vol. 20, (1982), pp. 573-580.

*Primary Examiner*—Mary C. Lee
*Assistant Examiner*—Peter Davis
*Attorney, Agent, or Firm*—Keil & Weinkauf

[57] ABSTRACT

Quinoline derivatives fused to a five-membered heterocyclic ring and of the formula

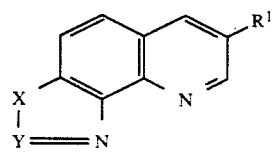

where
$R^1$ is hydrogen, halogen, carboxyl or substituted or unsubstituted alkyl,
Y is nitrogen or C—$R^2$, where
$R^2$ is hydrogen, halogen, hydroxyl, alkoxy, alkylthio, substituted or unsubstituted alkyl, substituted or unsubstituted cycloalkyl, substituted or unsubstituted benzyl, phenethyl, phenyl or naphthyl, or a substituted or unsubstituted 5- or 6-membered heterocyclic ring with one or two heteroatoms selected from the group consisting of oxygen, sulfur and nitrogen,
X is oxygen or N—$R^3$, $R^3$ being hydrogen, substituted or unsubstituted alkyl, alkenyl, alkynyl, cycloalkyl or subsituted or unsubstituted benzyl, processes for their manufacture and their use for combating unwanted plant growth.

6 Claims, No Drawings

DERIVATIVES OF QUINOLINE FUSED TO A FIVE-MEMBERED HETEROCYCLIC RING

The present invention relates to quinoline derivatives, herbicides containing these compounds as active ingredients, and a method for controlling undesired plant growth using these compounds.

Substituted 3H-imidazo[4,5-h]quinolines and oxazolo[5,4-h]quinolines are described in J. Fluorine Chem. 20 (1982) 573–580 and 41 (1988) 277–288. Substituted triazolo[5,4-h]quinolines are disclosed in Collect. Czech. Chem. Comm. 52 (1987) 2918–2925 and 53 (1988) 1068–1077. No herbicidal properties of the quinoline derivatives have been disclosed.

We have now found that derivatives of quinoline fused to a five-membered heterocyclic ring, of the formula I

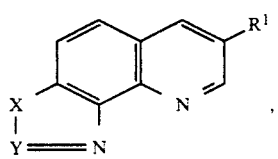

where
R$^1$ is hydrogen, halogen, carboxyl, or C$_1$–C$_6$-alkyl which is unsubstituted or substituted by C$_1$–C$_4$-alkoxy, C$_1$–C$_4$-alkylthio or halogen,
Y is nitrogen or C—R$^2$ where
R$^2$ is hydrogen, halogen, hydroxyl, C$_1$–C$_4$-alkoxy, C$_1$–C$_4$-alkylthio, or C$_1$–C$_6$-alkyl which is unsubstituted or substituted by halogen, hydroxyl, acetoxy, cyano, C$_1$–C$_4$-alkoxy or C$_1$–C$_4$-alkylthio, or C$_3$–C$_6$-cycloalkyl which is unsubstituted or substituted by C$_1$–C$_4$-alkyl, or benzyl, phenethyl, phenyl or naphthyl each of which is unsubstituted or substituted by nitro, amino, halogen, C$_1$–C$_4$-alkyl, C$_1$–C$_4$-alkoxy, C$_1$–C$_4$-alkylthio, C$_1$–C$_4$-haloalkyl, acylamino or acyloxy, or a 5- or 6-membered heterocyclic ring which has one or two hetero atoms selected from the group comprising oxygen, sulfur and nitrogen and is unsubstituted or substituted by nitro, C$_1$–C$_4$-alkyl or halogen,
X is oxygen or N—R$^3$ where R$^3$ is hydrogen, C$_1$–C$_6$-alkyl, C$_2$–C$_6$-alkenyl or C$_2$–C$_6$-alkynyl each of which is unsubstituted or substituted by halogen, amino, mono- or dialkylamino, hydroxyl, C$_1$–C$_4$-alkoxy or C$_1$–C$_4$-acyloxy, or C$_3$–C$_6$-cycloalkyl which is unsubstituted or substituted by C$_1$–C$_4$-alkyl, or benzyl which is unsubstituted or substituted by halogen, C$_1$–C$_4$-alkyl, C$_1$–C$_4$-haloalkyl or C$_1$–C$_4$-alkoxy,
have a herbicidal action and are selective with respect to crop plants.

The C$_1$–C$_6$-alkyls for R$^1$, R$^2$ and R$^3$ in formula I can be unbranched or branched and be, for example, methyl, ethyl, n-propyl, i-propyl, n-butyl, i-butyl, s-butyl, n-pentyl or n-hexyl. Corresponding statements apply to alkoxy, alkylthio, haloalkyl, alkylamino, hydroxyalkyl, alkoxyalkyl and acyloxyalkyl. Suitable substituents of the alkyls for R$^1$ and R$^2$ are halogen such as chlorine, bromine or fluorine, hydroxyl, such as hydroxymethyl or 1-hydroxyethyl, C$_1$–C$_4$-alkoxy or C$_1$–C$_4$-alkylthio, such as methoxy, ethoxy, methylthio or ethylthio. Examples of such radicals are trichloromethyl, difluoromethyl, trifluoromethyl, chloromethyl, methoxymethyl, 1-methoxyethyl, methylthiomethyl and ethylthiomethyl. Radicals with 1 to 4 carbon atoms are preferred.

Halogen in substituents of the formula I is, for example, fluorine, chlorine or bromine.

Examples of C$_3$–C$_6$-cycloalkyl for R$^2$ and R$^3$ are cyclopropyl, cyclobutyl, cyclopentyl and cyclohexyl. R$^2$ can also be substituted by C$_1$–C$_4$-alkyl, especially methyl or ethyl.

Benzyl, 1-phenethyl, 2-phenethyl, phenyl, 1-naphthyl and 2-naphthyl for R$^2$ can be substituted one or more times. Examples of substituents are nitro, amino, halogen such as fluorine, chlorine and bromine, C$_1$–C$_4$-alkyl, preferably methoxy or ethoxy, C$_1$–C$_4$-alkylthio, preferably methylthio, C$_1$–C$_4$-haloalkyl such as trifluoromethyl, acylamino with 1 to 4 carbon atoms in the acyl, for example formyl, acetyl, propionyl, n-butyryl or i-butyryl, and acyloxy with 2 to 5 carbon atoms in the acyl, for example acetyloxy, propionyloxy, n-butyryloxy or i-butyryloxy.

Examples of heterocyclic radicals for R$^2$ are pyrrolyl, furyl, thienyl, thiazolyl, isothiazolyl, oxazolyl, isoxazolyl, pyrazolyl, imidazolyl, pyridyl, pyrimidyl, pyrazinyl and pyridazinyl. These radicals can be substituted by nitro, C$_1$–C$_4$-alkyl, preferably methyl or ethyl, or by halogen such as chlorine, bromine or fluorine.

R$^3$ in —NR$^3$ is hydrogen, C$_1$–C$_6$-alkyl, preferably C$_1$–C$_4$-alkyl, especially methyl or ethyl, C$_2$–C$_6$-alkenyl, especially vinyl or allyl, C$_2$–C$_6$-alkynyl, especially propargyl, or C$_1$–C$_4$-alkyl which is unsubstituted or substituted by halogen, amino, mono-C$_1$–C$_4$ or di-C$_1$–C$_4$-alkylamino, hydroxyl, C$_1$–C$_4$-alkoxy or C$_1$–C$_4$-acyloxy, for example 2-chloroethyl, 3-chloro-n-propyl, 2-aminoethyl, 2-methylaminoethyl, 2-dimethylaminoethyl, 2-hydroxyethyl, 3-acetoxypropyl or 2-methoxypropyl, or benzyl which is unsubstituted or substituted by halogen, C$_1$–C$_4$-alkyl, C$_1$–C$_4$-haloalkyl or C$_1$–C$_4$-alkoxy, for example 4-chlorobenzyl, 4-trifluoromethylbenzyl, 4-methylbenzyl, 4-methoxybenzyl or 2,4-dichlorobenzyl.

The 3H-imidazo[4,5-h]quinolines of the formula I are obtained by reacting 7,8-diaminoquinolines of the formula

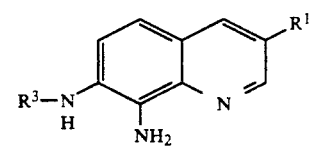

in a conventional manner with carboxylic acids of the formula R$^2$—COOH (III) or orthoesters of the formula R$^2$—C(OR$^4$)$_3$ (IV) where R$^4$ is C$_1$–C$_4$-alkyl.

The reaction takes place very satisfactorily at from 80° to 120° C. in the presence of polyphosphoric acid, at from 80° to 95° C. in hydrochloric acid of a variety of concentrations, or at from 70° to 100° C. with 3 to 6 equivalents of IV. The amount of III is expediently 1.1 mole for each 1 mole of II. Relatively large excesses of III have no adverse effects.

The oxazolo[5,4-h]quinolines of the formula I are obtained in a manner corresponding to that for 3H-imidazo[4,5-h]quinolines by reacting 7-hydroxy-8-aminoquinolines of the formula

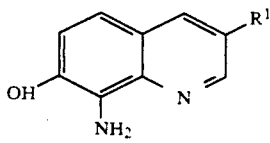

with carboxylic acids of the formula III or orthoesters of the formula IV. The reaction conditions are the same as indicated for the synthesis of the 3H-imidazo[4,5-h]-quinolines.

The triazolo[5,4-h]quinolines of the formula I are obtained by diazotization of 7,8-diaminoquinolines of the formula

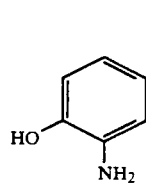

in a conventional manner.

The reaction takes place at from −10° to +10° C. in the presence of an acid, preferably sulfuric acid or hydrochloric acid.

The diaminoquinolines II and the aminohydroxyquinolines V can be obtained easily from 7-chloroquinolines of the formula VI where R¹ has the meanings specified for formula I. The synthesis is carried out in a conventional manner as shown in the scheme below:

a)

(VI) → → →

(II)

b)

(VI) →

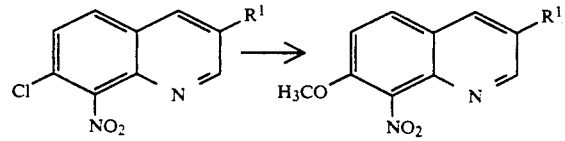

(V)

SYNTHESIS EXAMPLES

EXAMPLE 1

3-Methyl-7-chloro-3H-imidazo[4,5-h]quinoline 24.9 g (0.12 mol) of 8-amino-3-chloro-7-methylaminoquinoline and 107 g (0.72 mol) of triethyl orthoformate are heated at 100° C. for 30 min. The mixture is then cooled to 0° C., and the precipitate (32 g) is filtered off with suction. The mother liquor is concentrated under reduced pressure, and the residue is recrystallized from ethyl acetate/petroleum ether. The two solids obtained in this way are identical. Yield: 48.5 g (82%); melting point 188° to 189° C.

EXAMPLE 2

2-Methyl-3-ethyl-7-chloro-3H-imidazo[4,5-h]quinoline 14 g (64 mmol) of 8-amino-3-chloro-7-ethylaminoquinoline and 42 g (0.26 mol) of triethyl orthoacetate are stirred at 100° C. for 1 hour. The mixture is allowed to cool to room temperature, excess orthoester is evaporated off, and the residue is recrystallized from ethyl acetate.

Yield: 7.7 g (49%); melting point 145° to 148° C.

EXAMPLE 3

2-(4-Chlorophenyl)-3-ethyl-7-chloro-3H-imidazo[4,5-h]quinoline

A mixture of 4.1 g (20 mmol) of 8-amino-3-chloro-7-ethylaminoquinoline, 3.1 g (20 mmol) of 4-chlorobenzoic acid and 20 ml of polyphosphoric acid is heated at 120° C. for 1 hour. It is allowed to cool to 90° C., and 100 g of ice are slowly added to the solution. The mixture is then poured into 200 g of ice, and the pH is adjusted to 12 with concentrated sodium hydroxide solution. The precipitate is filtered off with suction, washed thoroughly with hot water, dried at 70° C. under reduced pressure and recrystallized from ethyl acetate.

Yield: 5.5 g (80%); melting point 110° to 112° C.

EXAMPLE 4

2,7-Dimethyloxazolo[5,4-h]quinoline 3.48 g (20 mmol) of 8-amino-7-hydroxy-3-methylquinoline and 16.2 g (100 mmol) of triethyl orthoacetate are heated at 100° C. for 1 hour. The reaction mixture is then allowed to cool to room temperature, 50 ml of petroleum ether are added while stirring vigorously, and the precipitate is filtered off with suction.

Yield: 3.05 g (77%); melting point 132° to 134° C.

EXAMPLE 5

2-(4-Chlorophenyl)-7-chloroxazolo[5,4-h]quinoline

A mixture of 3.89 g (20 mmol) of 8-amino-3-chloro-7-hydroxyquinoline, 3.44 g (22 mmol) of 4-chlorobenzoic acid and 20 ml of polyphosphoric acid is heated at 120° C. for 2 hours. It is allowed to cool to 90° C., and 100 g of ice and 500 ml of water are cautiously added. The resulting suspension is adjusted to pH 12 with concentrated sodium hydroxide solution, and the precipitate is filtered off with suction, washed with water until free of salts and dried at 60° C. under reduced pressure. Recrystallization from ethyl acetate yields 3.2 g (51%); melting point > 250° C.

EXAMPLE 6

3,7-Dimethyl-2-trifluoromethyl-3H-imidazo[4,5-h)quinoline

A mixture of 5.61 g (30 mmol) of 8-amino-3-methyl-7-methylaminoquinoline and 3.02 ml (40 mmol) of trifluoroacetic acid in 40 ml of 4N hydrochloric acid is heated at 95° C. for 2 h. It is then allowed to cool to room temperature and poured into 250 g of ice, the pH is adjusted to 9 with concentrated sodium hydroxide solution, and the precipitate is filtered off with suction. The crude product is dried and recrystallized from ethyl acetate/petroleum ether.

Yield: 4.8 g (63%); melting point 233°-235° C.

EXAMPLE 7

3-Ethyl-2-hydroxyimidazo[4,5-h]quinoline 22.4 g (0.12 mol) of 8-amino-7-ethylaminoquinoline and 9 g (0.15 mol) of urea are heated at 160° C. for 2 h, stirring vigorously. The mixture is allowed to cool to 140° C., and 50 ml of water are slowly added dropwise. After further cooling to 100° C., another 100 ml of water are added. The precipitate is filtered off with suction, washed again with hot water and dried under reduced pressure.

Yield: 21.6 g (85%); melting point > 250° C.

EXAMPLE 8

2,7-Dichloro-3-methylimidazo[4,5-h]quinoline 7 g (30 mmol) of 7-chloro-2-hydroxy-3-methylimidazo[4,5-h]quinoline are mixed with 7 g (33.6 mmol) of phosphorus pentachloride and 35 ml (0.38 mol) of phosphorus oxytrichloride. The mixture is refluxed for 15 h, then allowed to cool to room temperature and poured into 500 g of ice, the mixture is neutralized with concentrated sodium hydroxide solution, and the precipitate is filtered off with suction. Drying and recrystallization from ethanol result in 2.8 g (37%) of product; melting point 211° to 213° C.

The methods described in the synthesis examples are suitable, with appropriate modification of the starting compounds, for obtaining further compounds of the formula I. Examples of such compounds are listed in the tables which follow. Because their structures are closely related to those of the compounds mentioned in the synthesis examples, they are expected to have a similar action.

TABLE 1

| No. | R¹ | R² | R³ | mp [°C.] |
|---|---|---|---|---|
| 9 | H | H | CH₃ | 135–137 |
| 10 | H | CH₃ | CH₃ | 238–239 |
| 11 | H | CH(CH₃)₂ | CH₃ | 173–174 |
| 12 | H | cyclopropyl | CH₃ | — |
| 13 | H | 4-Cl-C₆H₄ | CH₃ | 209–211 |
| 14 | H | 3-Cl-C₆H₄ | CH₃ | — |
| 15 | H | 2-Cl-C₆H₄ | CH₃ | 205–207 |
| 16 | H | CH₂—OCH₃ | CH₃ | 112–114 |
| 17 | H | CH₂—SCH₃ | CH₃ | 153–155 |
| 18 | H | CH(CH₃)OCH₃ | CH₃ | 78–80 |

TABLE 1-continued

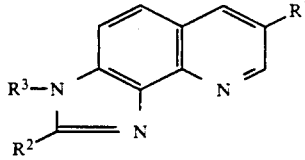

| No. | R¹ | R² | R³ | mp [°C.] |
|---|---|---|---|---|
| 19 | H | CH₂Cl | CH₃ | 78–80 |
| 20 | H | CHF₂ | CH₃ | 199–201 |
| 21 | H | CF₃ | CH₃ | 182–184 |
| 22 | H | OH | CH₃ | >250 |
| 23 | H | Cl | CH₃ | — |
| 24 | H | CH₃ | C₂H₅ | 150–153 |
| 25 | H | CH(CH₃)₂ | C₂H₅ | 58–61 |
| 26 | H | CH₃OCH₂ | C₂H₅ | 80–82 |
| 27 | H | CF₃ | C₂H₅ | 174–177 |
| 7 | H | OH | C₂H₅ | >250 |
| 28 | H | Cl | C₂H₅ | — |
| 29 | H | CH₃ | CH₂CH₂CH₃ | 109–111 |
| 30 | H | CH₃OCH₂ | CH₂CH₂CH₃ | oil |
| 31 | H | CF₃ | CH₂CH₂CH₃ | 190–192 |
| 32 | H | CH₃ | CH₂CH(CH₃)₂ | 105–108 |
| 33 | H | CHF₂ | CH₂CH(CH₃)₂ | 145–146 |
| 34 | H | CF₃ | CH₂CH(CH₃)₂ | 210–212 |
| 35 | H | CH₃ | cyclopropyl | 224–226 |
| 36 | H | CF₃ | cyclopropyl | — |
| 37 | H | CF₃ | CH=CH—CH₃ | 172–174 |
| 38 | H | CH₂Cl | CH₂CH₂OH | >250 |
| 39 | H | CH₂—OCH₃ | CH₂CH₂OH | 163–165 |
| 40 | H | CF₃ | CH₂CH₂Cl | 192–194 |
| 41 | H | CF₃ | CH₂CH₂CH₂OH | 132–135 |
| 42 | H | CF₃ | CH₂CH₂CH₂Cl | 173–175 |
| 43 | H | CF₃ | CH₂CH(CH₃)OH | 208–210 |
| 44 | H | CF₃ | CH₂CH(CH₃)Cl | 210–212 |
| 45 | H | CH₂Cl | CH₂CH(CH₃)OH | >250 |
| 46 | H | CH₂OCH₃ | CH₂CH(CH₃)OH | 143–145 |
| 47 | CH₃ | H | H | — |
| 48 | CH₃ | CH₃ | H | — |
| 49 | CH₃ | CH(CH₃)₂ | H | 92–95 |
| 50 | CH₃ | 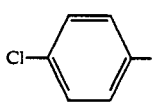 | H | — |
| 51 | CH₃ | 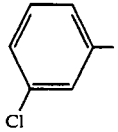 | H | 152–153 |
| 52 | CH₃ | 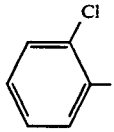 | H | — |
| 53 | CH₃ | CH₃ | CH₃ | 173–175 |
| 6 | CH₃ | CF₃ | CH₃ | 233–235 |
| 54 | CH₃ | CH₃ | C₂H₅ | 213–216 |
| 55 | CH₃ | CH(CH₃)₂ | C₂H₅ | 132–133 |
| 56 | C₂H₅ | CH₃ | CH₃ | 114–118 |
| 57 | C₂H₅ | CF₃ | CH₃ | 159–161 |
| 58 | CH(CH₃)₂ | CF₃ | CH₃ | 149–150 |
| 59 | Cl | H | H | — |
| 60 | Cl | CH₃ | H | 273–275 |
| 61 | Cl | CH(CH₃)₂ | H | 215 |
| 62 | Cl | 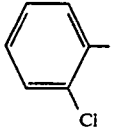 | H | 180–182 |

TABLE 1-continued

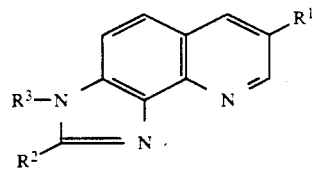

| No. | R¹ | R² | R³ | mp [°C.] |
|---|---|---|---|---|
| 63 | Cl | 3-chlorophenyl | H | 118–121 |
| 64 | Cl | 4-chlorophenyl | H | 116–119 |
| 65 | Cl | CF₃ | H | 234–239 |
| 1 | Cl | H | CH₃ | 188–189 |
| 66 | Cl | CH₃ | CH₃ | 167 |
| 67 | Cl | C₂H₅ | CH₃ | 98–101 |
| 68 | Cl | CH₂CH₂CH₃ | CH₃ | 129 |
| 69 | Cl | CH(CH₃)₂ | CH₃ | 142–144 |
| 70 | Cl | CH₂CH(CH₃)₂ | CH₃ | 113 |
| 71 | Cl | CH(CH₃)C₂H₅ | CH₃ | 126–128 |
| 72 | Cl | (CH₂)₅CH₃ | CH₃ | 128 |
| 73 | Cl | cyclopropyl | CH₃ | 48–50 |
| 74 | Cl | cyclobutyl | CH₃ | 143–145 |
| 75 | Cl | 2-methylcyclopropyl | CH₃ | 174–177 |
| 76 | Cl | cyclopentyl | CH₃ | 142–144 |
| 77 | Cl | benzyl | CH₃ | 194–196 |
| 78 | Cl | 2-chlorobenzyl | CH₃ | 209–211 |
| 79 | Cl | 3-chlorobenzyl | CH₃ | 161–163 |
| 80 | Cl | 4-chlorobenzyl | CH₃ | 170–173 |
| 81 | Cl | phenethyl (CH₂CH₂-phenyl) | CH₃ | 170–173 |
| 82 | Cl | 2-thienylmethyl | CH₃ | — |
| 83 | Cl | 3-thienylmethyl | CH₃ | — |

TABLE 1-continued

[Structure: quinoline with R¹ at 3-position, and at 7,8-positions an amidine group R³-N-C(R²)=N-]

| No. | R¹ | R² | R³ | mp [°C.] |
|---|---|---|---|---|
| 84 | Cl | 4-Cl-C₆H₄ | CH₃ | 170–172 |
| 85 | Cl | 3-Cl-C₆H₄ | CH₃ | 165–168 |
| 86 | Cl | 2-Cl-C₆H₄ | CH₃ | 231–232 |
| 87 | Cl | 2,4-Cl₂-C₆H₃ | CH₃ | >250 |
| 88 | Cl | 2,5-Cl₂-C₆H₃ | CH₃ | 238–240 |
| 89 | Cl | 3,5-Cl₂-C₆H₃ | CH₃ | 170–172 |
| 90 | Cl | 2-NO₂-C₆H₄ | CH₃ | — |
| 91 | Cl | 4-O₂N-C₆H₄ | CH₃ | — |
| 92 | Cl | 2-HO-C₆H₄ | CH₃ | — |

TABLE 1-continued

[Structure: quinoline with R¹ at position 3, R³-N at position 7, and R²-C=N fused at position 8]

| No. | R¹ | R² | R³ | mp [°C.] |
|---|---|---|---|---|
| 93 | Cl | 3-methoxyphenyl | CH₃ | 177–179 |
| 94 | Cl | 3-aminophenyl | CH₃ | 216–217 |
| 95 | Cl | 2-methylphenyl | CH₃ | — |
| 96 | Cl | 3,5-dimethylphenyl | CH₃ | 196–198 |
| 97 | Cl | 4-methylphenyl | CH₃ | 190–191 |
| 98 | Cl | 5-methylfuran-2-yl | CH₃ | — |
| 99 | Cl | furan-3-yl | CH₃ | 165 |
| 100 | Cl | 5-methylthien-2-yl | CH₃ | 95–96 |
| 101 | Cl | thien-3-yl | CH₃ | 204–205 |
| 102 | Cl | CH₂OCH₃ | CH₃ | 138–140 |
| 103 | Cl | CH₂OC₆H₅ | CH₃ | 237–240 |
| 104 | Cl | CH₂SCH₃ | CH₃ | 145–148 |
| 105 | Cl | CH₂Cl | CH₃ | >250 |
| 106 | Cl | CH₂CN | CH₃ | — |
| 107 | Cl | CH₂OC(O)CH₃ | CH₃ | — |
| 108 | Cl | CH(CH₃)OH | CH₃ | 65–66 |
| 109 | Cl | CH(CH₃)OCH₃ | CH₃ | 132–135 |
| 110 | Cl | CHF₂ | CH₃ | 215–216 |
| 111 | Cl | CHCl₂ | CH₃ | 110–115 |

TABLE 1-continued

| No. | R¹ | R² | R³ | mp [°C.] |
|---|---|---|---|---|
| 112 | Cl | CF₃ | CH₃ | 173–175 |
| 113 | Cl | CCl₃ | CH₃ | 247–250 |
| 114 | Cl | CONH₂ | CH₃ | >250 |
| 115 | Cl | SH | CH₃ | >250 |
| 116 | Cl | SCH₃ | CH₃ | 140–141 |
| 8 | Cl | Cl | CH₃ | 210–213 |
| 117 | Cl | OCH₃ | CH₃ | — |
| 118 | Cl | OC₂H₅ | CH₃ | 125–128 |
| 119 | Cl | CF₃ | CH=CH₂ | 125–128 |
| 2 | Cl | H | C₂H₅ | 215–217 |
| 120 | Cl | CH₃ | C₂H₅ | 145–148 |
| 121 | Cl | C₂H₅ | C₂H₅ | 138–140 |
| 122 | Cl | CH(CH₃)₂ | C₂H₅ | 127–130 |
| 123 | Cl | cyclopropyl | C₂H₅ | 146–148 |
| 124 | Cl | CH₂Cl | C₂H₅ | >250 |
| 125 | Cl | CH₂OCH₃ | C₂H₅ | 72–74 |
| 126 | Cl | CF₃ | C₂H₅ | 140–143 |
| 127 | Cl | OH | C₂H₅ | >250 |
| 128 | Cl | Cl | C₂H₅ | — |
| 129 | Cl | 2-chlorophenyl | C₂H₅ | 198 |
| 130 | Cl | 3-chlorophenyl | C₂H₅ | 155–156 |
| 3 | Cl | 4-chlorophenyl | C₂H₅ | 110–112 |
| 131 | Cl | 3-thienyl | C₂H₅ | 112–114 |
| 132 | Cl | H | CH₂CH₂CH₃ | 98–98 |
| 133 | Cl | CH₃ | CH₂CH₂CH₃ | 128–130 |
| 134 | Cl | CH₂OCH₃ | CH₂CH₂CH₃ | 142–144 |
| 135 | Cl | CF₃ | CH₂CH₂CH₃ | 178–181 |
| 136 | Cl | CH₃ | CH₂—CH=CH₂ | 138–140 |
| 137 | Cl | CH₃ | CH=CH—CH₃ | 234–236 |
| 138 | Cl | H | CH₂CH(CH₃)₂ | 111–113 |
| 139 | Cl | CH₃ | CH₂CH(CH₃)₂ | 123–125 |
| 140 | Cl | CF₃ | CH₂CH(CH₃)₂ | 152–155 |
| 141 | Cl | H | benzyl | 163 |
| 142 | Cl | CH₃ | benzyl | — |
| 143 | Cl | H | cyclopropyl | 130–132 |
| 144 | Cl | CH₃ | cyclopropyl | 229–231 |
| 145 | Cl | C₂H₅ | cyclopropyl | — |
| 146 | Cl | CHF₂ | cyclopropyl | 180–183 |
| 147 | Cl | CF₃ | cyclopropyl | — |
| 148 | Cl | H | cyclopentyl | — |
| 149 | Cl | CH₃ | cyclopentyl | 167–170 |
| 150 | Cl | CH₃ | CH₂CH₂OH | 245–247 |
| 151 | Cl | CH₂OCH₃ | CH₂CH₂OH | >250 |
| 152 | Cl | CF₃ | CH₂CH₂OH | 243–245 |
| 153 | Cl | CONH₂ | CH₂CH₂OH | >250 |
| 154 | Cl | OH | CH₂CH₂OH | 227–229 |

TABLE 1-continued

Structure: quinoline with R³-N(-C(R²)=N-) at position 7,8 and R¹ at position 3

| No. | R¹ | R² | R³ | mp [°C.] |
|-----|-----|-----|-----|-----|
| 155 | Cl | CH₃ | CH₂CH₂OC(O)CH₃ | resin |
| 156 | Cl | CH₂OCH₃ | CH₂CH(CH₃)OH | 190–192 |
| 157 | Cl | CF₃ | CH₂CH(CH₃)OH | 197–200 |
| 158 | Cl | OH | CH₂CH(CH₃)OH | 232–233 |
| 159 | Cl | CH₃ | CH₂CH(CH₃)OC(O)CH₃ | resin |
| 160 | Cl | CH₂OCH₃ | CH₂CH₂CH₂OH | 159–162 |
| 161 | Cl | CF₃ | CH₂CH₂CH₂OH | 150–153 |
| 162 | Cl | OH | CH₂CH₂CH₂OH | >250 |
| 163 | Cl | CF₃ | CH₂CH₂CH₂OC(O)CH₃ | 149–151 |
| 164 | Cl | CF₃ | CH₂CH₂Cl | 172–174 |
| 165 | Cl | CF₃ | CH₂CH(CH₃)Cl | 161–162 |
| 166 | Cl | OH | CH₂CH₂CH₂Cl | 213–215 |
| 167 | Cl | CH₂OCH₃ | CH₂CH₂N(CH₃)₂ | 170–171 |
| 168 | Cl | CF₃ | CH₂CH₂N(CH₃)₂ | 166–168 |

TABLE 2

Structure (Ib): quinoline with R²-C(=N-)-O- at position 7,8 and R¹ at position 3

| No. | R¹ | R² | mp [°C.] |
|-----|-----|-----|-----|
| 169 | H | CH₃ | 155–156 |
| 170 | H | C₂H₅ | 92–93 |
| 171 | Cl | H | 138 |
| 172 | Cl | CH₃ | 162–164 |
| 173 | Cl | 2-Cl-C₆H₄ | 164 |
| 174 | Cl | 3-Cl-C₆H₄ | 232 |
| 5 | Cl | 4-Cl-C₆H₄ | >250 |
| 175 | CH₃ | H | 115–117 |
| 4 | CH₃ | CH₃ | 132–134 |
| 176 | CH₃ | C₂H₅ | 79–80 |
| 177 | CH₃ | 2-Cl-C₆H₄ | 144–146 |
| 178 | CH₃ | 3-Cl-C₆H₄ | 130–131 |
| 179 | CH₃ | 4-Cl-C₆H₄ | 243–245 |
| 180 | H | H | — |
| 181 | H | CH₃ | 191–194 |
| 182 | H | C₂H₅ | 108–110 |
| 183 | H | n-C₃H₇ | 109–112 |
| 184 | H | i-C₄H₉ | 104–107 |
| 185 | H | c-C₃H₅ | 205–208 |
| 186 | CH₃ | CH₃ | 190–192 |
| 187 | C₂H₅ | CH₃ | 88–90 |
| 188 | Cl | H | >280 |
| 189 | Cl | CH₃ | 192–195 |
| 190 | Cl | C₂H₅ | 141–144 |

TABLE 2-continued (Ib)

[Structure: quinoline fused system with R¹ at position 3, OR² group, and N]

| No. | R¹ | R² | mp [°C.] |
|-----|-----|-----|----------|
| 191 | Cl | n-C₃H₇ | 145-148 |
| 192 | Cl | c-C₃H₅ | 103-107 |
| 193 | Cl | i-C₄H₉ | 145-150 |
| 194 | Cl | HOCH₂CH₂ | 222-224 |
| 195 | Cl | HOCH—CH₂<br>    \|<br>   CH₃ | 202-205 |
| 196 |  | HOCH₂CH₂CH₂ | 124-127 |
| 197 | Cl | ClCH₂CH₂CH₂ | 134-136 |
| 198 | Cl | AcO—CH₂CH₂ | 187-190 |

The quinoline derivatives I fused to a five-membered heterocyclic ring, or herbicidal agents containing them, may be applied for instance in the form of directly sprayable solutions, powders, suspensions (including high-percentage aqueous, oily or other suspensions), dispersions, emulsions, oil dispersions, pastes, dusts, broadcasting agents, or granules by spraying, atomizing, dusting, broadcasting or watering. The forms of application depend entirely on the purpose for which the agents are being used, but they must ensure as fine a distribution of the active ingredients according to the invention as possible.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as toluene, xylene, paraffin, tetrahydronaphthalene, alkylated naphthalenes and their derivatives, methanol, ethanol, propanol, butanol, cyclohexanol, cyclohexanone, chlorobenzene, isophorone, etc., and strongly polar solvents such as N,N-dimethylformamide, dimethyl sulfoxide, N-methylpyrrolidone, water, etc. are suitable.

Aqueous formulations may be prepared from emulsion concentrates, pastes, oil dispersions, wettable powders or water-dispersible granules by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of aromatic sulfonic acids, e.g., ligninsulfonic acid, phenolsulfonic acid, naphthalenesulfonic acid and dibutylnaphthalenesulfonic acid, and of fatty acids, alkyl and alkylaryl sulfonates, and alkyl, lauryl ether and fatty alcohol sulfates, and salts of sulfated hexadecanols, heptadecanols, and octadecanols, salts of fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin-sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acids, silica gels, silicates, talc, kaolin, attapulgus clay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain meals, bark meal, wood meal, and nutshell meal, cellulosic powders, etc.

The formulations contain from 0.1 to 95, and preferably 0.5 to 90, % by weight of active ingredient.

Examples of formulations are as follows:

I. 90 parts by weight of compound no. 93 is mixed with 10 parts by weight of N-methyl-alpha-pyrrolidone. A mixture is obtained which is suitable for application in the form of very fine drops.

II. 20 parts by weight of compound no. 36 is dissolved in a mixture consisting of 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

III. 20 parts by weight of compound no. 37 is dissolved in a mixture consisting of 40 parts by weight of cyclohexanone, 30 parts by weight of isobutanol, 20 parts by weight of the adduct of 7 moles of ethylene oxide and 1 mole of isooctylphenol, and 10 parts by weight of the adduct of 40 moles of ethylene oxide and 1 mole of castor oil. By pouring the solution into 100,000 parts by weight of water and finely distributing it therein, an aqueous dispersion is obtained containing 0.02% by weight of the active ingredient.

IV. 20 parts by weight of compound no. 60 is dissolved in a mixture consisting of 25 parts by weight of cyclohexanone, 65 parts by weight of a mineral oil fraction having a boiling point between 210° and 280° C., and 10 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

V. 20 parts by weight of compound no. 36 is well mixed with 3 parts by weight of the sodium salt of diisobutylnaphthalene-alpha-sulfonic acid, 17 parts by weight of the sodium salt of a lignin-sulfonic acid obtained from a sulfite waste liquor, and 60 parts by weight of powered silica gel, and triturated in a hammer mill. By uniformly distributing the mixture in 20,000 parts by weight of water, a spray liquor is obtained containing 0.1% by weight of the active ingredient.

VI. 3 parts by weight of compound no. 37 is intimately mixed with 97 parts by weight of particulate kaolin. A dust is obtained containing 3% by weight of the active ingredient.

VII. 30 parts by weight of compound no. 69 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 20 parts by weight of compound no. 63 is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

The active ingredients or the herbicidal agents containing them may be applied pre- or postemergence. If certain crop plants tolerate the active ingredients less well, application techniques may be used in which the herbicidal agents are sprayed from suitable equipment in such a manner that the leaves of sensitive crop plants are if possible not touched, and the agents reach the soil or the unwanted plants growing beneath the crop plants (post-directed, lay-by treatment).

The application rates depend on the objective to be achieved, the time of the year, the plants to be combated and their growth stage, and are from 0.001 to 4, preferably 0.01 to 2, kg of active ingredient per hectare.

To increase the spectrum of action and to achieve synergistic effects, the compounds I may be mixed with each other, or mixed and applied together with numerous representatives of other herbicidal or growth-regulating active ingredient groups. Examples of suitable components are diazines, 4H-3,1-benzoxazine derivatives, benzothiadiazinones, 2,6-dinitroanilines, N-phenylcarbamates, thiolcarbamates, halocarboxylic acids, triazines, amides, ureas, diphenyl ethers, triazinones, uracils, benzofuran derivatives, cyclohexane-1,3-dione derivatives, quinolinecarboxylic acids, (hetero)-aryloxyphenoxypropionic acids and salts, esters, amides thereof, etc.

It may also be useful to apply the herbicidal compounds I, either alone or in combination with other herbicides, in admixture with other crop protection agents, e.g., agents for combating pests or phytopathogenic fungi or bacteria. The compounds may also be mixed with solutions of mineral salts used to remedy nutritional or trace element deficiencies. Non-phytotoxic oils and oil concentrates may also be added.

In view of the numerous application methods possible, the compounds according to the invention may be used in a large number of crops. Those which follow are given by way of example:

| Botanical name | Common name |
| --- | --- |
| Allium cepa | onions |
| Ananas comosus | pineapples |
| Arachis hypogaea | peanuts (groundnuts) |
| Asparagus officinalis | asparagus |
| Avena sativa | oats |
| Beta vulgaris spp. altissima | sugarbeets |
| Beta vulgaris spp. rapa | fodder beets |
| Beta vulgaris spp. esculenta | table beets, red beets |
| Brassica napus var. napus | rapeseed |
| Brassica napus var. napobrassica | swedes |
| Brassica napus var. rapa | turnips |
| Brassica rapa var. silvestris | |
| Camellia sinensis | tea plants |
| Carthamus tinctorius | safflower |
| Carya illinoinensis | pecan trees |
| Citrus limon | lemons |
| Citrus maxima | grapefruits |
| Citrus reticulata | mandarins |
| Citrus sinensis | orange trees |
| Coffea arabica (Coffea canephora, Coffea liberica) | coffee plants |
| Cucumis melo | melons |
| Cucumis sativus | cucumbers |
| Cynodon dactylon | Bermudagrass |
| Daucus carota | carrots |
| Elais guineensis | oil palms |
| Fragaria vesca | strawberries |
| Glycine max | soybeans |
| Gossypium hirsutum (Gossypium arboreum, Gossypium herbaceum, Gossypium vitifolium) | cotton |
| Helianthus annuus | sunflowers |
| Helianthus tuberosus | Jerusalem artichoke |
| Hevea brasiliensis | rubber plants |
| Hordeum vulgare | barley |
| Humulus lupulus | hops |
| Ipomoea batatas | sweet potatoes |
| Juglans regia | walnut trees |
| Lactuca sativa | lettuce |
| Lens culinaris | lentils |
| Linum usitatissimum | flax |
| Lycopersicon lycopersicum | tomatoes |
| Malus spp. | apple trees |
| Manihot esculenta | cassava |
| Medicago sativa | alfalfa (lucerne) |
| Mentha piperita | peppermint |
| Musa spp. | banana plants |
| Nicotiana tabacum (N. rustica) | tobacco |
| Olea europaea | olive trees |
| Oryza sativa | rice |
| Panicum miliaceum | millet |
| Phaseolus lunatus | limabeans |
| Phaseolus mungo | mungbeans |
| Phaseolus vulgaris | snapbeans, green beans, dry beans |
| Pennisetum glaucum | pearl millet |
| Petroselinum crispum spp. tuberosum | parsley |
| Picea abies | Norway spruce |
| Abies alba | fir trees |
| Pinus spp. | pine trees |
| Pisum sativum | English peas |
| Prunus avium | cherry trees |
| Prunus domestica | plum trees |
| Prunus dulcis | almond trees |
| Prunus persica | peach trees |
| Pyrus communis | pear trees |
| Ribes sylvestre | redcurrants |
| Ribes uva-crispa | gooseberries |
| Ricinus communis | castor-oil plants |
| Saccharum officinarum | sugar cane |
| Secale cereale | rye |
| Sesamum indicum | sesame |
| Solanum tuberosum | Irish potatoes |
| Sorghum bicolor (s. vulgare) | sorghum |
| Sorghum dochna | sorgo |
| Spinacia oleracea | spinach |
| Theobroma cacao | cacao plants |
| Trifolium pratense | red clover |
| Triticum aestivum | wheat |
| Triticum durum | durum wheat |
| Vaccinium corymbosum | blueberries |
| Vaccinium vitis-idaea | cranberries |
| Vicia faba | tick beans |
| Vigna sinensis (V. unguiculata) | cow peas |
| Vitis vinifera | grapes |
| Zea mays | Indian corn, sweet corn, maize |

USE EXAMPLES

The herbicidal action of the 3H-imidazo[4,5-h](oxazolo[5,4-h])quinolines of the formula I is demonstrated in greenhouse experiments:

The vessels employed were plastic flowerpots having a volume of 300 cm$^3$ and filled with a sandy loam containing about 3.0% humus. The seeds of the test plants were sown separately, according to species.

For the postemergence treatment, plants were used which had been sown in the pots and grown there, or they were grown separately as seedlings and transplanted to the pots a few days before treatment.

The plants were grown, depending on growth form, to a height of 3 to 15 cm before being treated with the compounds, suspended or emulsified in water. The application rate for postemergence treatment was 1.0 kg/ha.

The pots were set up in the greenhouse, heat-loving species at 20° to 35° C., and species from moderate climates at 10° to 20° C. The experiments were run for from 2 to 4 weeks. During this period the plants were tended and their reactions to the various treatments assessed. The assessment scale was 0 to 100, 100 denoting nonemergence or complete destruction of at least the visible plant parts, and 0 denoting no damage or normal growth.

The plants used for the greenhouse experiments were *Cassia tora*, Ipomoea spp., and *Lamium amplexicaule*.

Active ingredient no. 1, applied postemergence at a rate of 1.0 kg/ha, provided excellent control of unwanted broadleaved plants and was tolerated by the crop plant Indian corn.

The herbicidal action of triazolo[5,4-h]quinolines of the formula I on the growth of test plants is demonstrated by the following greenhouse experiments.

The vessels employed were plastic flowerpots having a volume of 300 cm$^3$ and filled with a sandy loam containing about 3.0% humus. The seeds of the test plants were sown separately, according to species.

For the preemergence treatment, the formulated active ingredients were applied to the surface of the soil immediately after the seeds had been sown. The compounds were emulsified or suspended in water as vehicle, and sprayed through finely distributing nozzles.

After the agents had been applied, the vessels were lightly sprinkler-irrigated to induce germination and growth. Transparent plastic covers were then placed on the vessels until the plants had taken root. The cover ensured uniform germination of the plants, insofar as this was not impaired by the active ingredients.

For the postemergence treatment, plants were used which had been sown in the pots and grown there, or they were grown separately as seedlings and transplanted to the pots a few days before treatment. The plants were grown, depending on growth form, to a height of 3 to 15 cm before being treated with the compounds, suspended or emulsified in water.

The pots were set up in the greenhouse, heat-loving species at 20° to 35° C., and species from moderate climates at 10° to 25° C. The experiments were run for from 2 to 4 weeks. During this period the plants were tended and their reactions to the various treatments assessed. The assessment scale was 0 to 100, 100 denoting nonemergence or complete destruction of at least the visible plant parts, and 0 denoting no damage or normal growth.

The plants used in the greenhouse experiments were *Chenopodium album* and *Stellaria media*.

Compounds 191 and 192, applied postemergence at a rate of 2.0 kg/ha, provided excellent control of unwanted broadleaved plants.

We claim:

1. Quinoline derivatives of the formula I

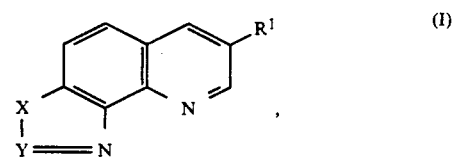

where
R$^1$ is hydrogen, halogen, carboxyl, or C$_1$-C$_6$-alkyl which is unsubstituted or substituted by C$_1$-C$_4$-alkoxy, C$_1$-C$_4$-alkylthio or halogen.

Y is nitrogen or C—R$^2$, where

R$^2$ is hydrogen, halogen, hydroxyl, C$_1$-C$_4$-alkoxy, C$_1$-C$_4$-alkylthio, or C$_1$-C$_6$-alkyl which is unsubstituted or substituted by halogen, hydroxyl, acetoxy, cyano, C$_1$-C$_4$-alkoxy or C$_1$-C$_4$-alkylthio, or is C$_3$-C$_6$-cycloalkyl which is unsubstituted or substituted by C$_1$-C$_4$-alkyl, or is benzyl, phenethyl, phenyl or naphthyl, each of which is unsubstituted or substituted by nitro, amino, halogen, C$_1$-C$_4$-alkyl, C$_1$-C$_4$-alkoxy, C$_1$-C$_4$-alkylthio, C$_1$-C$_4$-haloalkyl, acylamino or acyloxy or a pyrrolyl, furyl, thienyl, thiazolyl, isothiazolyl, oxazolyl, isoxazolyl, pyrazolyl, or imidazolyl, heterocyclic ring which is unsubstituted or substituted by nitro, C$_1$-C$_4$-alkyl or halogen, X is oxygen or N—R$^3$, where R$^3$ is hydrogen, C$_1$-C$_6$-alkyl, C$_2$-C$_6$-alkenyl or C$_2$-C$_6$-alkynyl, each of which is unsubstituted or substituted by halogen, amino, mono- or dialkylamino, hydroxyl, C$_1$-C$_4$-alkoxy or C$_1$-C$_4$-acyloxy, or is C$_3$-C$_6$-cycloalkyl which is unsubstituted or substituted by C$_1$-C$_4$-alkyl, or is benzyl which is unsubstituted or substituted by halogen, C$_1$-C$_4$-alkyl, C$_1$-C$_4$-haloalkyl or C$_1$-C$_4$-alkoxy, with the proviso that R$^2$ is not hydrogen, methyl, trifluoromethyl, phenyl or benzyl when Y is C—R$^2$, R$^1$ is hydrogen and X is NH, and R$^2$ is not hydrogen, methyl or trifluoromethyl when X is N—R$^3$ and R$^3$ is n-benzyl or n-butyl; and further with the proviso that R$^1$ and R$^3$ are not simultaneously hydrogen when X=NR$^3$ and Y=N.

2. The quinoline derivative of the formula I as set forth in claim 1, where R$^1$ is halogen-substituted C$_1$-C$_4$-alkyl or halogen and Y is C—R$^2$.

3. The quinoline derivative of the formula I as set forth in claim 1, where R$^1$ is halogen-substituted C$_1$-C$_4$-alkyl or halogen, Y is C—R$^2$ and X is NR$^3$.

4. The quinoline derivative of claim 3, wherein R$^3$ is C$_1$-C$_6$-alkyl unsubstituted or substituted by halogen, amino, mono- or dialkylamino, hydroxyl, C$_1$-C$_4$-alkoxy or C$_1$-C$_4$-acyloxy.

5. A herbicidal composition which comprises inert additives and a quinoline derivative of the formula I

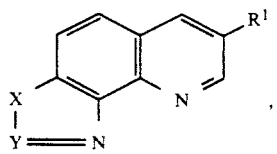

(I)

where
R$^1$ is hydrogen, halogen, carboxyl, or C$_1$-C$_6$-alkyl which is unsubstituted or substituted by C$_1$-C$_4$-alkoxy, C$_1$-C$_4$-alkylthio or halogen.

Y is nitrogen or C—R$^2$, where

R$^2$ is hydrogen, halogen, hydroxyl, C$_1$-C$_4$-alkoxy, C$_1$-C$_4$-alkylthio, or C$_1$-C$_6$-alkyl which is unsubstituted or substituted by halogen, hydroxyl, acetoxy, cyano, C$_1$-C$_4$-alkoxy or C$_1$-C$_4$-alkylthio, or is C$_3$-C$_6$-cycloalkyl which is unsubstituted or substituted by C$_1$-C$_4$-alkyl, or is benzyl, phenethyl, phenyl or naphthyl, each of which is unsubstituted or substituted by nitro, amino, halogen, C$_1$-C$_4$-alkyl, C$_1$-C$_4$-alkoxy, C$_1$-C$_4$-alkylthio, C$_1$-C$_4$-haloalkyl, acylamino or acyloxy or a pyrrolyl, furyl, thienyl, thiazolyl, isothiazolyl, oxazolyl, isoxazolyl, pyrazolyl, or imidazolyl, heterocyclic ring which is unsubstituted or substituted by nitro, C$_1$-C$_4$-alkyl or halogen, is oxygen or N—R$^3$, where R$^3$ is hydrogen, C$_1$-C$_6$-alkyl, C$_2$-C$_6$-alkenyl, or C$_2$-C$_6$-alkynyl, each of which is unsubstituted or substituted by halogen, amino, mono- or dialkylamino, hydroxyl, C$_1$-C$_4$-alkoxy or C$_1$-C$_4$-acyloxy, or is C$_3$-C$_6$-cycloalkyl which is unsubstituted or substituted by C$_1$-C$_4$-alkyl, or is benzyl which is unsubstituted or substituted by halogen, C$_1$-C$_4$-alkyl, C$_1$-C$_4$-haloalkyl or C$_1$-C$_4$-alkoxy, with the proviso that R$^2$ is not hydrogen, methyl, trifluoromethyl, phenyl or benzyl when Y is C—R$^2$, R$^1$ is hydrogen and X is NH, and R$^2$ is not hydrogen, methyl or trifluoromethyl when X is N—R$^3$ and R$^3$ is n-benzyl or n-butyl, and further with the proviso that R$^1$ and R$^3$ are not simultaneously hydrogen when X=NR$^3$ and Y=N.

6. A process for combating the growth of unwanted plants, wherein the plants and/or their habitat are treated with a herbicidally effective amount of a herbicidal composition which comprises inert additives and a quinoline derivative of the formula I

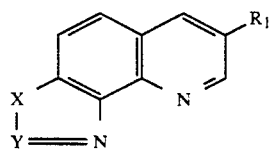

R$^1$ is hydrogen, halogen, carboxyl, or C$_1$-C$_6$-alkyl which is unsubstituted or substituted by C$_1$-C$_4$-alkoxy, C$_1$-C$_4$-alkylthio or halogen.

Y is nitrogen or C—R$^2$, where

R$^2$ is hydrogen, halogen, hydroxyl, C$_1$-C$_4$-alkoxy, C$_1$-C$_4$-alkylthio, or C$_1$-C$_6$-alkyl which is unsubstituted or substituted by halogen, hydroxyl, acetoxy, cyano, C$_1$-C$_4$-alkoxy or C$_1$-C$_4$-alkylthio, or is C$_3$-C$_6$-cycloalkyl which is unsubstituted or substituted by C$_1$-C$_4$-alkyl, or is benzyl, phenethyl, phenyl or naphthyl, each of which is unsubstituted or substituted by nitro, amino, halogen, C$_1$-C$_4$-alkyl, C$_1$-C$_4$-alkoxy, C$_1$-C$_4$-alkylthio, C$_1$-C$_4$-haloalkyl, acylamino or acyloxy or a pyrrolyl, furyl, thienyl, thiazolyl, isothiazolyl, oxazolyl, isoxazolyl, pyrazolyl, imidazolyl, pyridyl, pyrimidyl, pyrazinyl or pyridazinyl heterocyclic ring which is unsubstituted or substituted by nitro, C$_1$-C$_4$-alkyl or halogen, X is oxygen or N—R$^3$, where R$^3$ is hydrogen, C$_1$-C$_6$-alkyl, C$_2$-C$_6$-alkenyl, or C$_2$-C$_6$-alkynyl, each of which is unsubstituted or substituted by halogen, amino, mono- or dialkylamino, hydroxyl, C$_1$-C$_4$-alkoxy or C$_1$-C$_4$-acyloxy, or is C$_3$-C$_6$-cycloalkyl which is unsubstituted or substituted by C$_1$-C$_4$-alkyl, or is benzyl which is unsubstituted or substituted by halogen, C$_1$-C$_4$-alkyl, C$_1$-C$_4$-haloalkyl or C$_1$-C$_4$-alkoxy, with the proviso that R$^2$ is not hydrogen, methyl, trifluoromethyl, phenyl or benzyl when Y is C—R$^2$, R$^1$ is hydrogen and X is NH, and R$^2$ is not hydrogen, methyl or trifluoromethyl when X is N—R$^3$ and R$^3$ is n-benzyl or n-butyl, and further with the proviso that R$^1$ and R$^3$ are not simultaneously hydrogen when X=NR$^3$ and Y=N.

* * * * *

UNITED STATES PATENT AND TRADEMARK OFFICE
CERTIFICATE OF CORRECTION

PATENT NO. : 5,167,695

DATED : December 1, 1992

INVENTOR(S) : BRILL et al.

It is certified that error appears in the above-identified patent and that said Letters Patent is hereby corrected as shown below:

Claim 5, column 25, line 27: "or halogen, is oxygen" should read
-- or halogen, X is oxygen --

Signed and Sealed this

Twenty-first Day of December, 1993

Attest:

BRUCE LEHMAN

Attesting Officer          Commissioner of Patents and Trademarks